United States Patent [19]

Uehara et al.

[11] Patent Number: 4,928,172
[45] Date of Patent: May 22, 1990

[54] ENDOSCOPE OUTPUT SIGNAL CONTROL DEVICE AND ENDOSCOPE APPARATUS MAKING USE OF THE SAME

[75] Inventors: Masao Uehara; Akinobu Uchikubo; Katsuyuki Saito; Masahide Kanno; Jun Hasegawa; Masahiko Sasaki; Katsuyoshi Sasagawa; Shinji Yamashita, all of Tokyo, Japan

[73] Assignee: Olympus Optical Co., Ltd., Tokyo, Japan

[21] Appl. No.: 244,777

[22] Filed: Sep. 15, 1988

[30] Foreign Application Priority Data

Jan. 7, 1988 [JP] Japan .................. 63-001845

[51] Int. Cl.⁵ .................. H04N 7/18; H04N 5/52; A61B 1/06
[52] U.S. Cl. .................. 358/98; 358/174; 128/6
[58] Field of Search .................. 358/98, 174; 128/4, 128/6

[56] References Cited

U.S. PATENT DOCUMENTS

| | | | |
|---|---|---|---|
| 4,532,918 | 8/1985 | Wheeler | 358/98 |
| 4,535,758 | 8/1985 | Longacre et al. | 358/98 |
| 4,633,304 | 12/1986 | Nagasaki | 358/98 |

FOREIGN PATENT DOCUMENTS 61-61588 3/1986 Japan .

Primary Examiner—John K. Peng
Attorney, Agent, or Firm—Armstrong, Nikaido, Marmelstein, Kubovcik & Murray

[57] ABSTRACT

An endoscope using a solid state imaging device characterized by comprising a solid state imaging device capable of imaging an object image, a light emitting means giving an illuminating light to said object, a first level detecting means fed with a video signal from said solid state imaging device and detecting the level of this signal, a first level comparing means comparing the detected level of this detecting means and a preset first reference level with each other and outputting a first control signal corresponding to the level difference, a light adjusting means fed with this first control signal and adjusting the illuminating light from said light emitting means on the basis of this signal, a gain variable amplifying means taking in the video signal from the detecting end in said first level detecting means and amplifying it, a second level detecting means detecting the level of the signal from this amplifying means and a circuit means comparing the detected level of this detecting means and a preset second reference level with each other, forming a second control signal corresponding to the level difference and making this signal a gain controlling signal to said amplifying means.

22 Claims, 13 Drawing Sheets

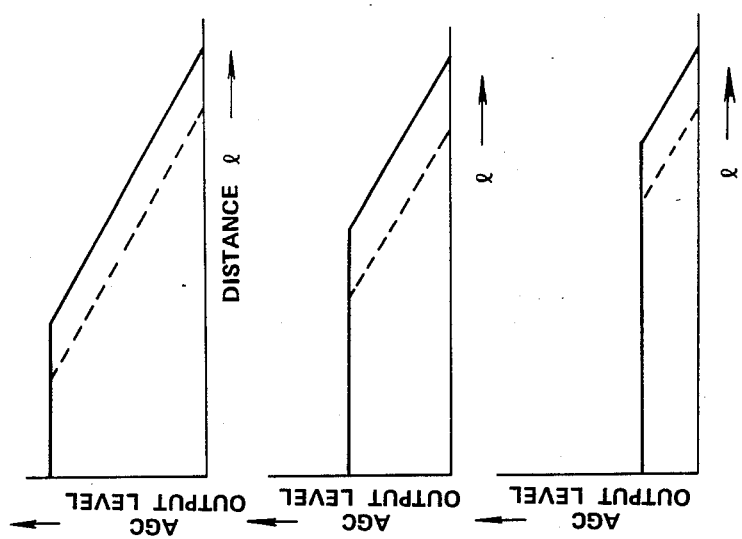

FULL-OPEN PERIOD

CONTRAST → TRANSMITTED LIGHT QUANTITY SMALL
TRANSMITTED LIGHT QUANTITY LARGE
$E_1$   $E_2$   $E$ ($V_{RMS}$)

ENDOSCOPE OUTPUT SIGNAL CONTROL DEVICE AND ENDOSCOPE APPARATUS MAKING USE OF THE SAME

BACKGROUND OF THE INVENTION

1. Field of the Invention

The present invention relates to an endoscope output signal control device having a means for controlling the quantity of light impinging upon an imaging means which picks up an endoscopic image. The invention also is concerned with an endoscope apparatus which makes use of such an endoscope output signal control device.

2. Related Art Statement

In recent years, electronic endoscopes have been put into practical use and incorporate, as an imaging means, solid-state imaging devices such as CCDs (Charge Coupled Device). This type of endoscope also is referred to as an "electronic scope".

Electronic scopes hitherto proposed, however, suffer a common disadvantage in that the dynamic range is restricted when compared with conventional optical endoscopes.

Under this circumstance, the present inventor has proposed, in Japanese Unexamined Patent Publication 61-61588, an improved electronic endoscope apparatus which expands the dynamic range which is restricted by the solid-state imaging device and which realizes high-speed control with good response to a change in the intensity of the light reflected from an object. This electronic endoscope uses, as a light control means, an electric control means so as to attain high-speed control and expand the dynamic range.

This electronic endoscope will be described in more detail with reference to FIG. 23.

White light from a lamp 3 of a light source unit 2 is made to pass through a light control means 4 such as an iris capable of controlling the light quantity and is then changed into a parallel light beam having a small diameter as it passes through optical lenses 5 and 6. This fine parallel light beam is made to pass through a rotary color filter 8 which is rotatingly driven by a motor 7. The light beam is converged by a condenser lens 9 so as to impinge upon the light incidence end of a light guide 12 of an electronic scope 11. The rotary color filter 8 has a disk-shaped filter frame having three sector-shaped openings to which are attached color filters capable of transmitting light of red, green and blue colors, respectively. As the color filter 8 rotates, red, green and blue color filters are successively brought into the path of the illuminating light so that illuminating light of red, green and blue colors (referred to as sequential light) are successively and sequentially applied to the light incident end of the light guide 12. The operation speed of the motor 7 which drives the rotary color filter 8 is controlled at a predetermined level by means of a servo circuit 14.

The light guide 12 sequentially transmits the sequential light so that the light emanates from the emanating end of an elongated insert section 15 of the endoscope so as to impinge upon the object 17 through a light distribution lens 16.

The sequential light reflected by the illuminated object 17 is focused through an objective lens 18 on the end of the insert section 15 on a solid-state imaging device (referred to as "SID" hereinafter) such as a CCD which is disposed on the focal plane of the objective lens 18. The thus formed image is photoelectrically converted so that an electrical signal corresponding to the optical image is obtained. The electrical signal is read in accordance with a drive signal which is applied from a drive circuit (not shown) to the SID 19 and is amplified by an amplifier 21. The amplified signal is delivered to a signal processing device (referred to as "video processor") 22 having the light source unit 2 and a signal processing means.

The electrical signal input to the video processor 22 is delivered through a first level detection means 23 to one of the input terminals of a first comparator means 24. The first level detection means 23 detects the output level corresponding to the level of the electrical signal. The electrical signal derived from the first level detection means 23, serving as a brightness information signal and applied to one of the input terminals of the first comparator means 24, is compared with a reference signal Vr1 applied to the other input terminal of the comparator means 24, whereby the brightness of the object image represented by the electrical signal is compared with a reference brightness represented by the reference signal Vr1. The output from the first comparator means 24, serving as a light quantity control signal, is delivered to a light control means 4 which is disposed between the lamp 3 and the lens 5 so as to control the opening of the iris thereby controlling the quantity of the light passed to the lens 5. More specifically, when the level of the electrical signal input to the first comparator means 24 is higher than the level of the reference signal Vr1, i.e., when the object image is brighter than the reference brightness, the iris opening is decreased to reduce the quantity of light by an amount corresponding to the difference in the brightness. Conversely, when the object image is darker than the reference brightness, the light control is conducted such as to increase the quantity of the light.

Thus, the light quantity control is executed in three steps: namely, (a) picking up the change in the intensity of the light reflected by the object, (b) detecting the change in the light intensity as a change in the output from the SID 19 and (c) controlling the change in the output as a change in the light quantity. These steps (a), (b) and (c) are executed in a closed loop sequentially and cyclically and the automatic light control (ALC) function is performed upon completion of each cycle in accordance with the change in the light reflected from the object, so as to optimally control the quantity of the illuminating light.

Thus, the level of the output from the amplifier 21 is controlled by the ALC function and is input to a signal processing circuit 27 through a variable gain amplifier 26. The signal processing circuit 27 is capable of temporarily storing the sequential red, green and blue signals and reading these signals simultaneously so as to form simultaneous red, green and blue signals. Then, suitable correcting operations such as gamma correction are executed on the simultaneous signals and the thus processed simultaneous signals are delivered to a TV monitor 28, whereby a color image of the object is formed on the TV monitor 28.

The output from the variable gain amplifier 26 is delivered to one of the input terminals of a second comparator means 30 after passing through a second level detection means 29 so as to be compared with a reference level Vr2 which is received by the other input terminal of the second comparator means 30, so that the second comparator means 30 delivers a signal corresponding to the result of the comparison.

For instance, when the level of the output from the variable gain amplifier 26 received by the second comparator means 30 is greater than reference level Vr2, the second comparator means 30 produces a signal for controlling the variable gain amplifier 26 so as to reduce the level of the output therefrom. Thus, the second comparator means performs a cyclic operation similar to that performed by the first comparator means 24, by an electrical gain correction means. With this arrangement, it is possible to elevate the output signal level so as to enable the observer to easily observe an image brightness level of which is still below a predetermined acceptable level even when the light control means 4 has been operated by the ALC such as to fully open the iris. In general, the light control means 4 controlled by the ALC circuit is composed of a mechanical iris motor and iris blades and generally exhibits a low response speed, but is capable of reducing any fluctuation on the TV monitor 28 by virtue of subsequent electrical correcting operation. In fact, the electrical correction means provides a remarkable effect in improving the quality of the image.

The known arrangement shown in FIG. 23 is so designed that the ALC function is always active and operative. A more practical arrangement therefore has been proposed as shown in FIG. 24.

In the arrangement shown in FIG. 24, the reference voltage Vr1 applied to the first comparator means 24 of the circuit shown in FIG. 23 is forcibly changed in accordance with light quantity control step so as to allow the light quantity control of the light control means 4 to be set manually.

In general, endoscopic diagnosis encounters a large change in the intensity of light reflected by the object (upper digestive organs and upper digestive system) depending on the portion of the object under diagnosis and other factors. It is difficult to optimize the light quantity over the entire part of the object with the known SID having a restricted dynamic range. A doctor as the user therefore has to delicately control the light quantity applied to the portion of the object which requires a minute check. The manual setting function afforded by the arrangement shown in FIG. 24 copes well with such a demand. More specifically, referring to FIG. 24, a light control switch SW 31 is disposed on, for example, a front panel which accommodates a signal processing device 22. The light control switch SW 31 comprises a light quantity up switch 32a and a light quantity down switch SW 32b. These switches SW 32a and SW 32b are connected to a CPU 34 via an input port 33. Each of these switches is set such that it delivers a signal of "H" level by a resistor R when it is in an off state. However, as the switch is turned on, the output level is changed to "L" which is delivered to the CPU 34 through the input port 33.

The CPU 34 is connected through a data BUS and an address BUS to a ROM 35 which stores program contents and information necessary for execution of the programs and is connected to a RAM 36 which provides a working area for the execution of the program. The CPU 34 also is connected to a programmable timer 37 so as to output frequency data corresponding to the operation of the light control switch SW 31 input through the input port 33. The output of the programmable interval timer 37 is input to a frequency/voltage (F/V) conversion circuit 38 so as to be converted into a voltage proportional to the frequency. This voltage is input to a differential amplifier 39 which computes the difference between this voltage and the reference level Vr1. The difference is input to the other input terminal of the first comparator means 24. Other portions of the arrangement shown in FIG. 24 are materially the same as those of the circuit shown in FIG. 23.

Thus, the circuit shown in FIG. 24 allows the reference level into the first comparator means 24 to be freely set at any desired level, thus providing an ALC which enables the light quantity to be set at any desired level.

For instance, if the output level of the F/V converter 38 is set at "0", the circuit shown in FIG. 24 operates in the same manner as the arrangement shown in FIG. 23.

Conversely, if the output of the F/V converter 38 is set at a level higher than "0", the differential amplifier 39 produces an output of a level lower than the reference level Vr1, so that the ALC functions such as to attain a light quantity corresponding to this low level output. Namely, the iris opening is reduced to decrease the light quantity.

Conversely, the light quantity is increased when the output from the F/V converter 38 is smaller than 0.

The level of the output of the F/V converter 38 can be set by means of the light quantity control switch SW 31.

For instance, when the up switch SW 32a is pressed, the resulting information is input to the CPU 34 through the input port 33. The CPU 34 then executes a routine as shown in FIG. 25. Namely, the CPU 34 writes a predetermined set frequency value in the programmable interval timer 37 such that the timer frequency is lowered by one stage. The set frequency value is stored in the ROM 35. In consequence, the programmable interval timer 37 in which the set frequency value is written produces a frequency signal which is one stage lower than the preceding frequency signal. The frequency signal now output from the programmable interval timer 37 is converted into voltage by the F/V converter 38 and the thus obtained voltage is input to a differential amplifier 39 which produces the difference between the input voltage signal and the reference level Vr1. The differential output from the differential amplifier 39 constitutes the reference level to be input to the first comparator means 24. The reference level in this state is one stage higher than the preceding reference level and the ALC operates to raise the light quantity level to this higher reference level. Thus, the operation is the same as that obtained when the command level is changed in one cycle of operation of the ALC circuit. In other words, it is possible to vary the state of the light control means 4 even when the level of the output from the first level detection means 23 is the same. For instance, the light control means 4 operates to increase the light quantity when the up switch SW 32a is pressed.

As will be understood from the foregoing description, the electronic endoscope apparatus shown in FIG. 24 can expand the detactable range between bright and dark objects having small and large reflectivity levels and can operate with a high response speed, by virtue of the provision of the ALC circuit and the electrical automatic gain control means (referred to as "AGC" hereafter). The endoscope apparatus shown in FIG. 24, however, suffers from the following problem. In some cases, a doctor as the observer wishes to lower the brightness of the object portion under examination for the purpose of minute examination when the image of the object portion is too bright to observe. In such a case, the doctor operates the light control switch SW 31 so as to reduce the light quantity set by the ALC. Unfortunately, however, the AGC operates so as to maintain the output therefrom at a constant level insofar as the output level set by the ALC falls within the range controllable by the AGC. It is therefore impossible to lower the level of brightness of the image on the monitor TV. This problem is not so serious when the brightness level is around the center step of the light control but is critical when the brightness is near the brightest or the darkest step, as will be understood from the following description taken in conjunction with FIGS. 26A and 26B. FIG. 26A illustrates the relationship between the light quantity steps and the illumination light quantity or the amount of exposure of the SID 19 controlled by the light control means 4. It will be seen that the relationship is substantially linear.

FIG. 26B shows the output level obtained through the AGC circuit as obtained when the AGC circuit is operated while the light quantity control step is changed. As will be seen from these Figures, the output level is changed along the solid-line curve due to the operation of the AGC circuit even when the light quantity is changed by the light control means. Thus, the signal level is fixed despite a change in the light quantity control step, in the insensitive range in which the AGC operates.

SUMMARY OF THE INVENTION

Accordingly, an object of the present invention is to provide an endoscope output signal control device which can provide both an enlarged dynamic range and higher speed of response to change in the light quantity, without causing any unfavorable effect on the light quantity controlling function, as well as an endoscope apparatus incorporating such an endoscope output signal control device.

Another object of the present invention is to provide an endoscope output signal control device which is capable of maintaining the brightness of the image at a level near each control limit of the automatic light control means substantially at a constant level even when the set level of the brightness is changed, as well as an endoscope apparatus incorporating such an endoscope output signal control device.

To these ends, according to one aspect of the present invention, there is provided an endoscope output signal control device comprising: a light quantity varying device capable of varying the quantity of light incident to an imaging device for forming an endoscopic image; light quantity setting device for variably setting the quantity of the incident light by driving the light quantity varying device; an automatic gain control device for conducting control so as to maintain the signal from the imaging device substantially at a constant level; and; automatic gain control eliminating device capable of eliminating, at least when the level of the signal from the imaging device is within a range controllable by the light quantity varying device, any influence of the automatic gain control device on the change in the level of the signal caused by a change in the level of light quantity set by the light quantity setting device. Preferably, the endoscope output signal control device of the invention further comprises automatic light control device capable of driving the light quantity varying device so as to control the quantity of the incident light in such a manner as to maintain the signal from the imaging device substantially at a constant level.

The invention also provides an endoscope apparatus incorporating the output signal control device, the apparatus comprising, in addition to the features of the output signal control device, an endoscope unit including an elongated insert section having an observation window at its end and a focusing optical system for receiving the light reflected from the object through the observation window so as to focus the light from the object, an imaging device for forming the image focused by the focusing optical system, a signal processing device for processing signals from the imaging device, and an illuminating device for supplying illuminating light to the field of vision of the image focusing system.

These and other objects, features and advantages of the present invention will become clear from the following description of the preferred embodiments when the same is read in conjunction with the accompanying drawings.

BRIEF DESCRIPTION OF THE DRAWINGS

FIGS. 5(A) to 5(C) are diagram showing the relationship between the AGC output characteristic and a change in the distance as realized by the embodiment shown in FIG. 1;

DETAILED DESCRIPTION OF THE PREFERRED EMBODIMENTS

Figure 1:
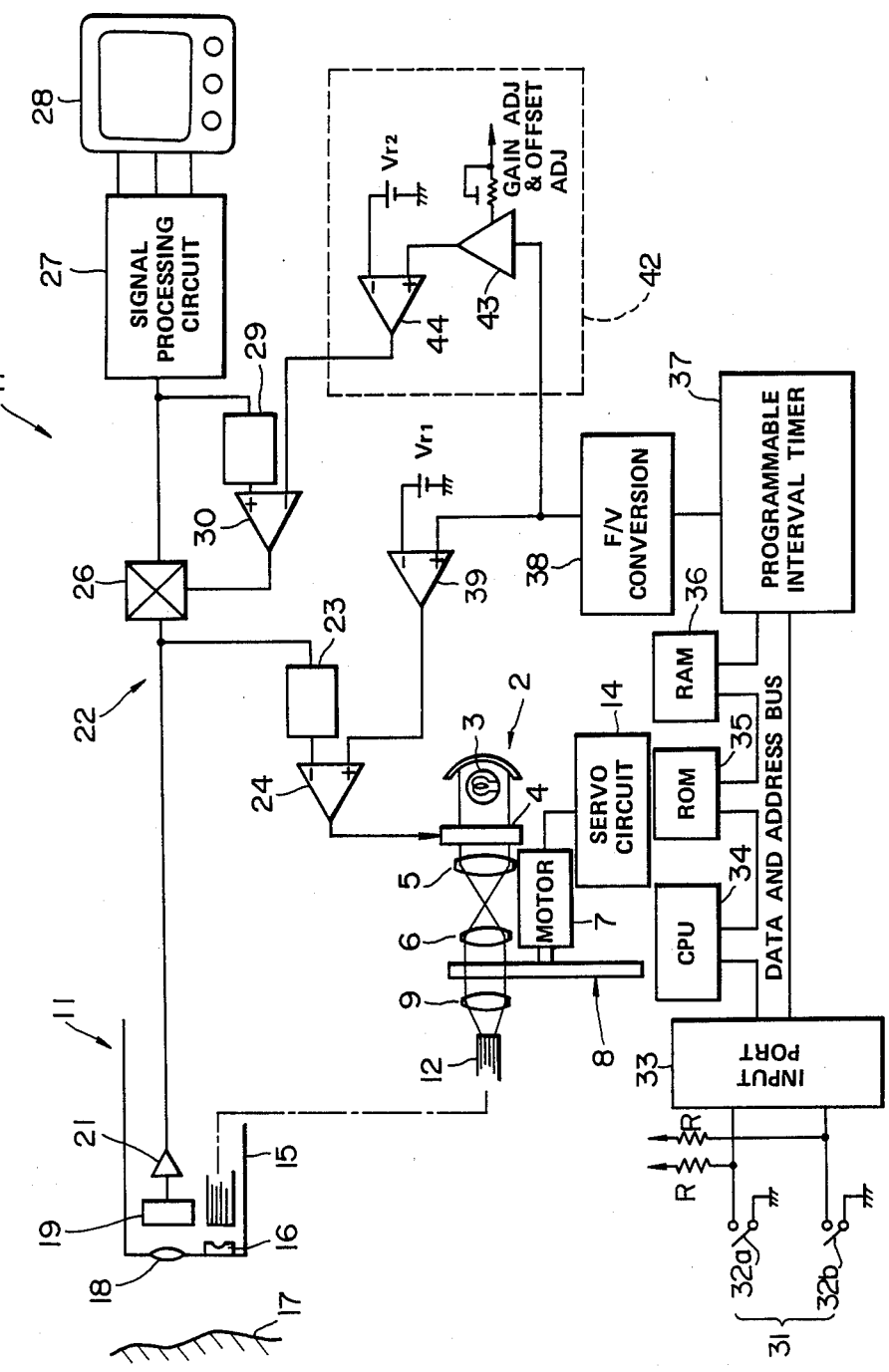
FIG. 1 is a block diagram of a first embodiment of the endoscope output signal control device in accordance with the present invention.

A first embodiment of the present invention will be described hereinunder with reference to FIGS. 1 to 6.

An electronic endoscope apparatus 41 has an electronic scope 11 including an elongated insert section 15, a signal processing device (video processor) detachably connected to the electronic scope and having an endoscope output signal control device, and a TV monitor 28 connected to the signal processing device 22.

The signal processing device 22 includes a light source section 2.

White light from a lamp 3 of a light source unit 2 is made to pass through a light control means 4 such as an iris capable of controlling the light quantity and is then changed into a parallel light beam having a small diameter as it passes through optical lenses 5 and 6. This fine parallel light beam is made to pass through a rotary color filter 8 which is rotatingly driven by a motor 7 and is converged by a condenser lens 9 so as to impinge upon the light incidence end of a light guide 12 of an electronic scope 11. The rotary color filter 8 has a disk-shaped filter frame having three sector-shaped openings to which are attached color filters capable of transmitting light of red, green and blue colors, respectively. As the color filter 8 rotates, red, green and blue color filters are successively brought into the path of the illuminating light so that illuminating light of red, green and blue colors (referred to as sequential light) are successively and sequentially applied to the light incident end of the light guide 12. The operation speed of the motor 7 which drives the rotary color filter 8 is controlled at a predetermined level by means of a servo circuit 14.

The light guide 12 sequentially transmits the sequential light so that the light emanates from the emanating end of an elongated insert section 15 of the endoscope so as to impinge upon the object 17 through a light distribution lens 16.

The sequential light reflected by the illuminated object 17 is focused through an objective lens 18 on the end of the insert section 15 on a solid-state imaging device (referred to as "SID" hereinafter) 19 such as a CCD which is disposed on the focal plane of the objective lens 18. The thus formed image is photoelectrically converted so that an electrical signal corresponding to the optical image is obtained. The electrical signal is read in accordance with a drive signal which is applied from a drive circuit (not shown) to the SID 19 and is amplified by an amplifier 21. The amplified signal is delivered to a signal processing device (referred to as "video processor") 22 having the light source unit 2 and a signal processing means.

The electrical signal input to the video processor 22 is delivered through a first level detection means 23 to one of input terminals of a first comparator means 24. The first level detection means 23 detects the output level corresponding to the level of the electrical signal. The electrical signal derived from the first level detection means, serving as a brightness information signal and applied to one of the input terminals of the first comparator means 24 is compared with a reference signal Vr1 applied to the other input terminal of the comparator means 24, whereby the brightness of the object image represented by the electrical signal is compared with a reference brightness represented by the reference signal Vr1. The output from the first comparator means 24, serving as a light quantity control signal, is delivered to a light control means 4 which is disposed between the lamp 3 and the lens 5 so as to control the opening of the iris thereby controlling the quantity of the light passed to the lens 5. More specifically, when the level of the electrical signal input to the first comparator means 24 is higher than the level of the reference signal Vr1, i.e., when the object image is brighter than the reference brightness, the iris opening is decreased to reduce the quantity of light by an amount corresponding to the difference in the brightness. Conversely, when the object image is darker than the reference brightness, the light control is conducted such as to increase the quantity of the light.

Thus, the light quantity control is executed in three steps: namely, (a) picking up the change in the intensity of the light reflected by the object, (b) detecting the change in the light intensity as a change in the output from the SID 19 and (c) controlling the change in the output as a change in the light quantity. These steps (a), (b) and (c) are executed in a closed loop sequentially and cyclically and the automatic light control (ALC) function is performed upon completion of each cycle in accordance with the change in the light reflected from the object, so as to optimally control the brightness of the illuminating light.

Thus, the level of the output from the amplifier 21 is controlled by the ALC function and is input to a signal processing circuit 27 through a variable gain amplifier 26. The signal processing circuit 27 is capable of temporarily storing the sequential red, green and blue signals and reading these signals simultaneously so as to form simultaneous red, green and blue signals. Then, suitable correcting operations such as gamma correction are executed on the simultaneous signals and the thus processed simultaneous signals are delivered to a TV monitor 28, whereby a color image of the object is formed on the TV monitor 28.

The output from the variable gain amplifier 26 is delivered to one of the input terminals of a second comparator means 30 after passing through a second level detection means 29 so as to be compared with a reference level Vr2 which is received by the other input terminal of the second comparator means 30, so that the second comparator means 30 delivers a signal corresponding to the result of the comparison.

For instance, when the level of the output from the variable gain amplifier 26 received by the second comparator means 30 is greater than reference level Vr2, the second comparator means 30 produces a signal for controlling the variable gain amplifier 26 so as to reduce the level of the output therefrom. Thus, the second comparator means performs a cyclic operation similar to that performed by the first comparator means 24, by an electrical gain correction means. With this arrangement, it is possible to elevate the output signal level so as to enable the observer to easily observe an image the brightness level of which is still below a predetermined acceptable level even when the light control means 4 has been operated by the ALC such as to fully open the iris. In general, the light control means 4 controlled by the ALC circuit is composed of a mechanical iris motor and iris blades and generally exhibits a low response speed, but is capable of reducing any fluctuation on the TV monitor 28 by virtue of subsequent electrical correcting operation. In fact, the electrical correction means provides a remarkable effect in improving the quality of the image.

In this embodiment, the light control also can be done manually. Namely, the reference voltage Vr1 applied to the first comparator means 24 of ALC circuit and the reference voltage Vr2 applied to the second comparator means 30 in the AGC circuit are forcibly changed in accordance with light quantity control step so as to allow the light quantity control to be done manually.

In general, endoscopic diagnosis encounters a large change in the intensity of light reflected by the object (upper digestive organs and upper digestive system) depending on the portion of the object under diagnosis and other factors. It is difficult to optimize the light quantity over the entire part of the object with the known SID 19 having a restricted dynamic range. A doctor as the user therefore has to delicately control the light quantity applied to the portion of the object which requires a minute check. The manual setting function easily complies with such a demand. More specifically, referring to FIG. 1, a light control switch SW 31 is disposed on, for example, a front panel which accommodates a signal processing means 22. The light control switch SW 31 comprises a light quantity up switch 32a and a light quantity down switch SW 32b. These switches SW 32a and SW 32b are connected to a CPU 34 via an input port 33. Each of these switches is set such that it delivers a signal of "H" level by a resistor R when it is in an off state. However, as the switch is turned on, the output level is changed to "L" which is delivered to the CPU 34 through the input port 33.

The CPU 34 is connected through a data BUS and an address BUS to a ROM 35 which stores program contents and information necessary for execution of the programs and is connected to a RAM 36 which provides a working area for the execution of the program. The CPU 34 also is connected to a programmable interval timer 37 so as to output frequency data corresponding to the operation of the light control switch SW 31 input through the input port 33. The output of the programmable interval timer 37 is input to a frequency/voltage (F/V) conversion circuit 38 so as to be converted into a voltage proportional to the frequency. This voltage is input to a differential amplifier 39 which computes the difference between this voltage and the reference level Vr1. The difference is input to the other input terminal of the first comparator means 24.

Thus, the described circuit allows the reference level into the first comparator means 24 to be freely set at any desired level, thus providing an ALC which enables the light quantity to be set at any desired level.

Figure 3:
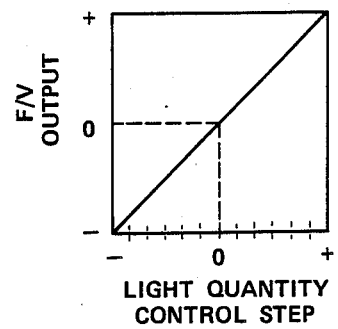
FIG. 3 is a diagram showing the relationship between the light quantity control steps and level of output from an F/V converter.

The change in the output from the F/V converter 38 is adjustable by a light control switch 31. FIG. 3 shows the output characteristic of the F/V converter in relation to the light quantity control steps. As will be seen from this Figure, the F/V output characteristic of + (plus) potential is obtained when the light control switch SW 31 is turned to the UP side. For the purpose of simplifying the explanation, it is assumed here that this polarity and conversion gain are determined by restrictions posed by the ALC circuit. This assumption, however, is only illustrative. For instance, it is not always necessary that the output of the F/V converter changes its polarity between + (plus) and − (minus).

The output from the F/V converter 38 is made to pass through a reference voltage generating circuit 42 and is then applied as an AGC reference voltage to the reference input terminal of the second comparator means 30.

Figure 2:
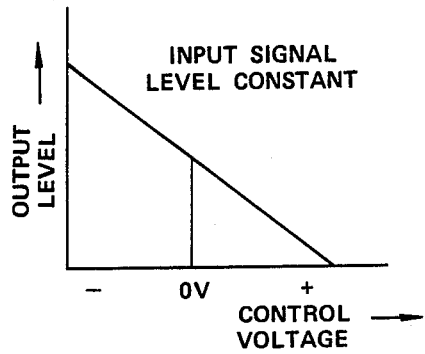
FIG. 2 is a diagram showing the relationship between a control voltage applied to a gain control terminal of a variable gain amplifier used in the embodiment shown in FIG. 1 and the level of the output signal from the variable gain amplifier.

FIG. 2 shows the control characteristic of the variable gain amplifier 26 used in this embodiment.

The reference voltage generating circuit 42 has an amplifier 43 for amplifying the output signal from the F/V converter 38 and a subtractor 44 having an input terminal (non-inversion input terminal) for receiving the output from the amplifier 43 and another input terminal (inversion input terminal) for receiving the reference level Vr2.

The gain and the offset of the amplifier 43 are adjusted such that the output signal from the F/V converter 38 matches for the control system of the AGC loop. For instance, the amplifier 43 amplifies the output signal from the F/V converter 38 by a gain $G_1$ and provides an offset $OFS_1$ so as to produce an output F/V OUT$\times G_1+OFS_1$. This signal is delivered to the subtractor 44 so as to be subtracted from the reference level Vr2 so that the reference input terminal of the second comparator means 30 receives a signal V44 which is represented by V44=Vr2−(F/V OUT$\times G_1+OFS_1$).

The output from the F/V converter 38, having the + (plus) polarity, is supplied through the amplifier 43 to the subtractor 44 so as to have a polarity which serves to reduce the control voltage of the variable gain amplifier 26. Since the variable gain amplifier 26 has a characteristic that the output level increases as the control voltage becomes lower, the + (plus) output from the F/V converter 38 serves to increase the output level of the variable gain amplifier 26.

The rate of increase of the output of the variable gain amplifier 26 preferably coincides with the rate of change of the signal level at the input terminal of the amplifier 26 to the light quantity control step, i.e., VI step/V center. This can be accomplished by a suitable setting of the gain at the amplifier 43.

The operation of the AGC circuit system described before can be regarded as a servo loop as will be understood from the following description.

Figure 4:
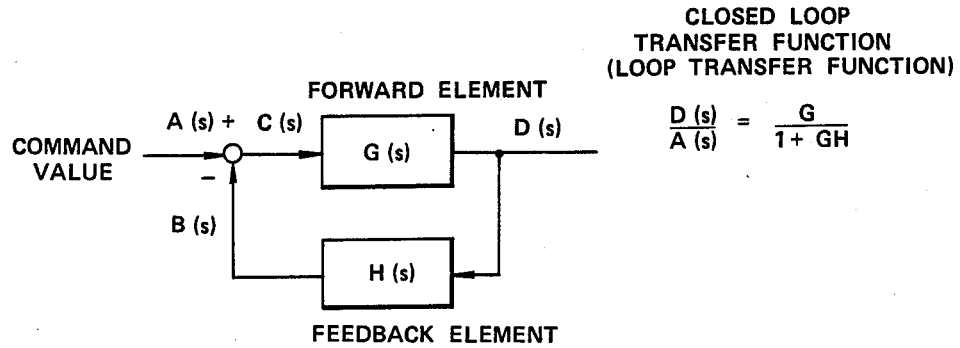
FIG. 4 is an illustration of a closed loop transmission function of an AGC circuit incorporated in the embodiment shown in FIG. 1.

FIG. 4 is a block diagram and transfer function of the AGC circuit system when the AGC circuit system is considered as being a servo loop.

The reference voltage generating circuit 42 shown in FIG. 1 generates the reference voltage as the difference between the reference level Vr2 and the light quantity control step generated by the amplifier 43. The thus formed reference voltage corresponds to the command value A(s) shown in FIG. 4.

Thus, the level of output of the automatic gain control means is corrected so as to unlimitedly approach the command value by the transfer function $D(s)/A(s)=G/(1+GH)$.

The change in the reference voltage V44 by the change in the light quantity control step appears as a change in the command value A(s) which serves to raise or lower the level of output from the automatic gain control means.

The operation of the AGC circuit in the first embodiment will be explained with reference to FIG. 5.

When the light control step has been set at bright level in the described embodiment, if the distance is increased as illustrated in FIG. 5(A), the output level is maintained constant over the greater distance because the gain of the variable gain amplifier 26 is increased.

Figure 6A:
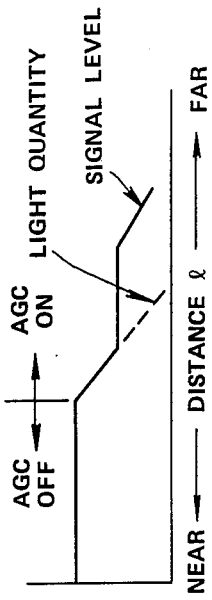
FIGS. 6(A) to 6(C) are diagrams showing, for the purpose of comparison with the operation characteristic of the embodiment shown in FIG. 1, the relationship between the AGC output characteristic and the change in distance as observed when the command of the AGC is fixed.

In contrast, in the conventional arrangement in which the command value of the AGC is fixed regardless of the change in the light quantity control step and the AGC is allowed to operate only after the light control means 4 such as iris has been fully opened, the output level drastically drops after the full opening of the light control means 4 as shown by solid line in FIG. 6(a) due to the operation of the AGC circuit.

Conversely, when the light quantity control step has been set at a dark level in the described embodiment, the output level does not rise and a constant output level is maintained over a longer distance by virtue of reduction in the gain of the variable gain amplifier 26.

Figure 6B:
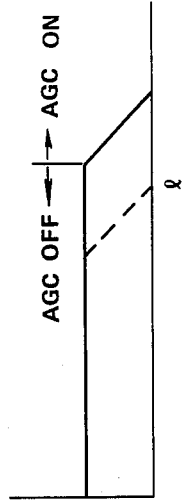
Figure 6C:
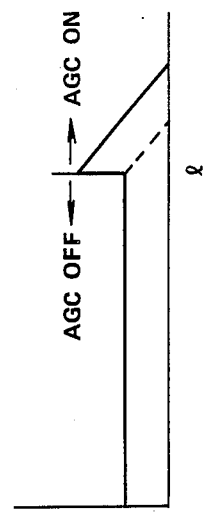

In contrast, in the known arrangement in which the command value of the AGC circuit is fixed regardless of the change in the light quantity control step, the AGC is turned on so as to cause a drastic rise of the output level as shown in FIG. 6(C).

When the central light quantity control step has been selected, the described embodiment maintains a constant output level over a longer distance as shown in FIG. 5(B).

Similar characteristic is obtained also in the conventional arrangement in which the command value of the AGC circuit is fixed regardless of a change in the light quantity control step, as will be seen from FIG. 6(B).

In FIGS. 6(A) and 6(C), the broken-line curves show amounts of change in the quantity of light emitted from the light source unit 2.

In the described embodiment, there is no insensitive range which is the range in which the signal level cannot be changed in response to a change in the light quantity control step under operation of the ALC and AGC circuits.

As will be seen from the foregoing description, the automatic light control (ALC) loop and the automatic gain control (AGC) loop are operatively connected by a simple construction to the means for externally controlling the intensity of the illuminating light to be applied to the object, thus ensuring the safe functioning of the external light quantity control so as to widen the observation range to enable darker and brighter objects to be observed, while attaining a high speed of response so as to ensure a quick change in the light quantity in response to a change in the light quantity control step.

Figure 7:
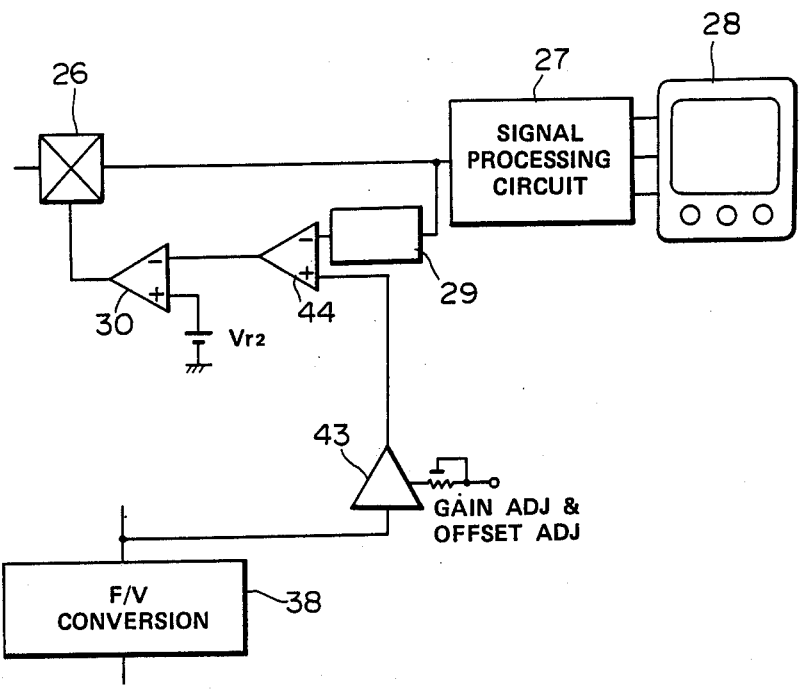
FIG. 7 is a block diagram showing an AGC circuit and elements around this circuit in a second embodiment of the present invention.
Figure 23:
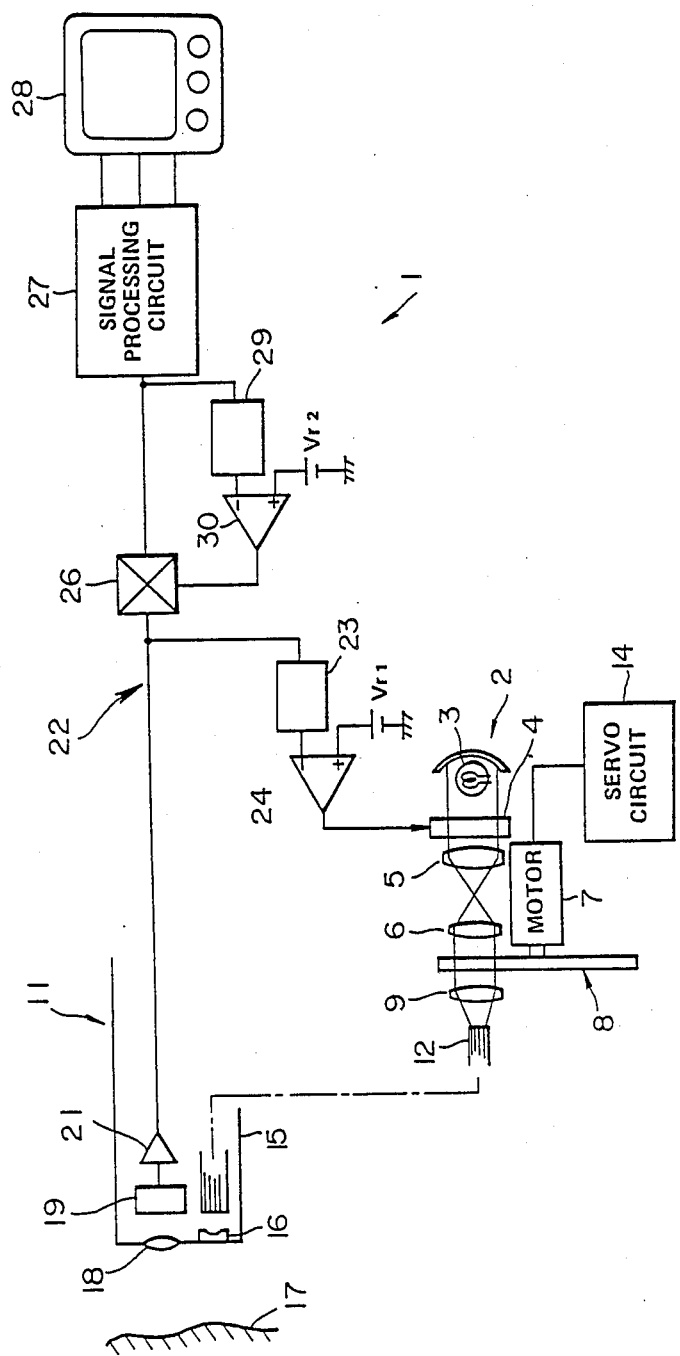
FIG. 23 is a block diagram showing the construction of a known endoscope apparatus.
Figure 24:
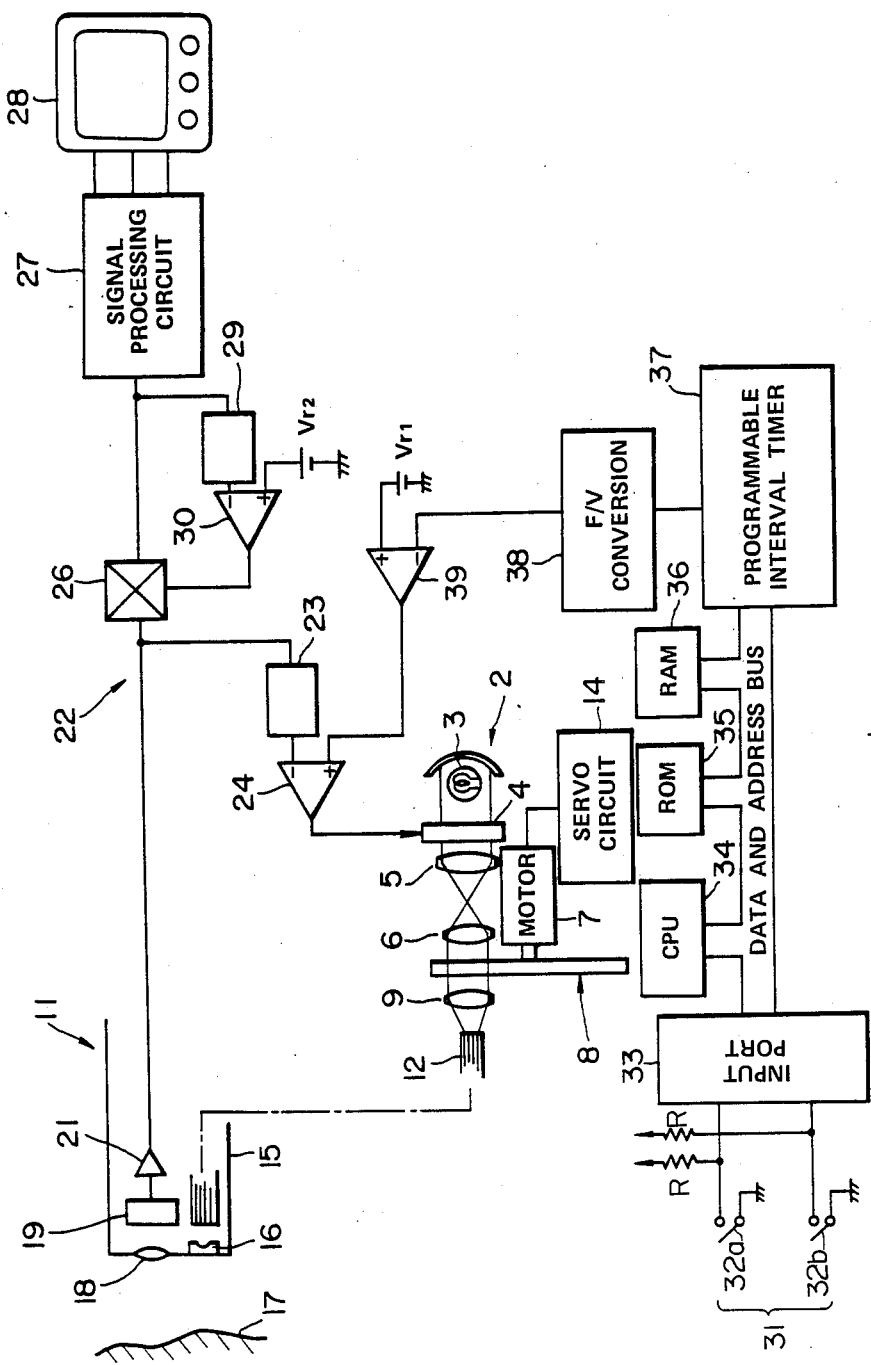
FIG. 24 is a block diagram showing the construction of another known endoscope apparatus which is an improvement in the apparatus shown in FIG. 23.
Figure 25:
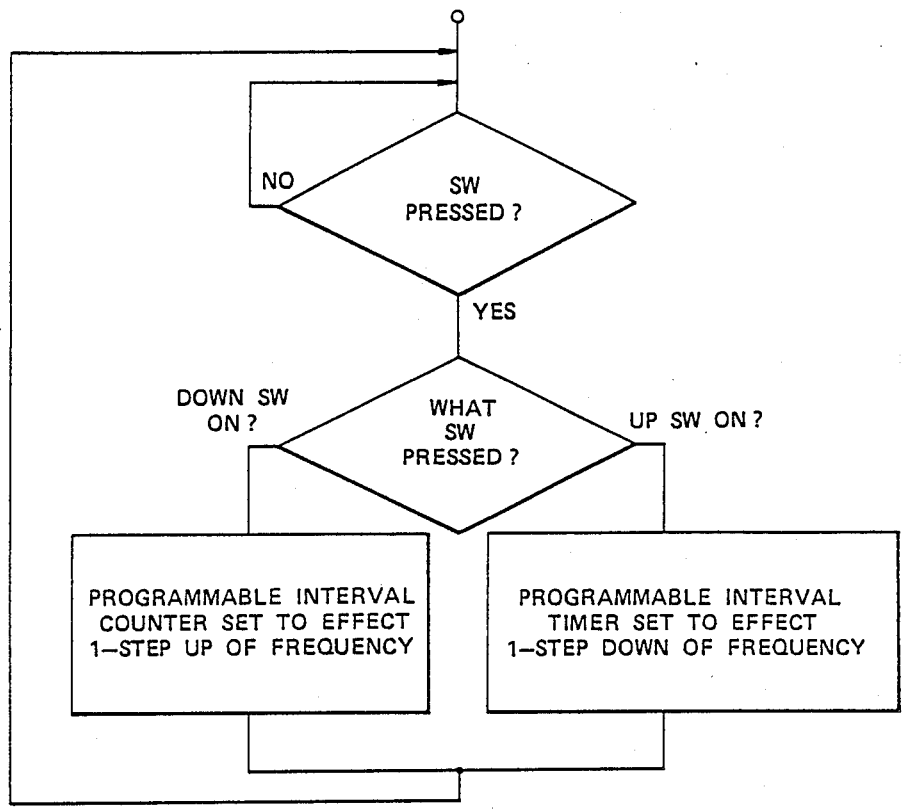
FIG. 25 is a flow chart showing a processing routine for conducting light control in the device shown in FIG. 24.
Figure 26A:
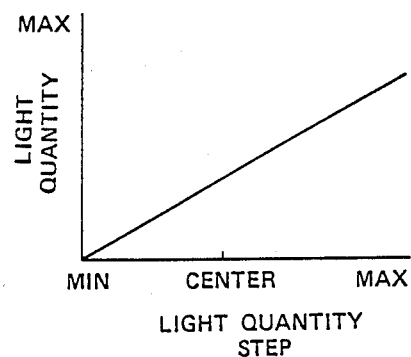
FIG. 26(A) is a chart showing the relationship between the light control steps and the light quantity.
Figure 26B:
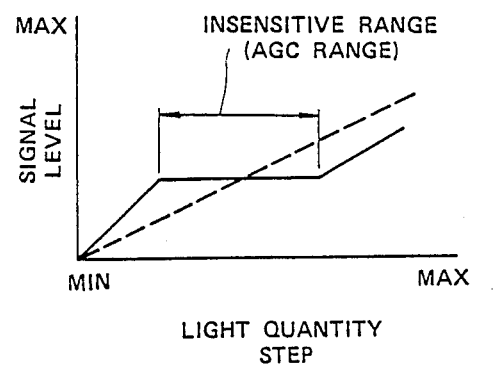
FIG. 26(B) is a chart showing the relationship between light control steps and signal level.

Thus, in the electronic endoscope apparatus of the invention, a function is provided in addition to the functions of the arrangement of FIG. 23 for allowing a manual control of the illuminating light quantity and for allowing the control of the gain of the AGC circuit in response to the manual control of the illuminating light quantity, so as to prevent the AGC circuit from conducting the control of the illuminating light quantity, thereby making it possible to obtain an object image with any desired quantity of the illuminating light. This feature enables a minute observation or check of an object when the described endoscope apparatus is used for medical diagnostic purposes. FIG. 7 shows a second embodiment of the present invention. This embodiment has a construction similar to that of the first embodiment shown in FIG. 1 and features a subtractor 44 connected between the second level detection means 29 and the second comparator means 30. The subtractor 44 receives, at its one input terminal (inversion input terminal) the output from the second level detection means 29, while the other input terminal (non-inversion terminal) receives the output from the amplifier 43. The inversion input terminal of the second comparator means 30 receives the output from the subtractor 44, while the reference input terminal (non-inversion input terminal) receives the reference level Vr2.

As will be clearly understood from FIG. 4, the loop transfer function is expressed as $D(s)/H(s)=G/(1+GH)$. This expression means that the output level of the automatic gain control means can be varied even if the feedback element H(s) is changed. The second embodiment, therefore, is constructed such that the offset voltage of the feedback element H(s) is varied in accordance with a change in the light quantity control step. Basically, however, the operation of the second embodiment is equivalent to that performed by the first embodiment when a disturbance is applied to the loop in the first embodiment. Thus, the first embodiment is more preferable than the second embodiment, as will be clear to those skilled in the art.

The control characteristic of the variable gain amplifier and the F/V conversion output in the second embodiment are shown in FIGS. 2 and 3, respectively. Thus, the control characteristic of the variable gain amplifier and the output of the F/V converter are materially the same as those in the first embodiment.

The operation of the whole apparatus also is materially the same as that of the first embodiment.

However, in the second embodiment, the loop performs correction to make the output unlimitedly approach the command value because the operation is equivalent to that performed when a disturbance is applied. The amount of correction is generally represented by the inverse of the loop gain, i.e., 1/(loop gain). It is therefore necessary to obtain a level which overcomes this correction amount by considerably increasing the gain of the amplifier 43.

Figure 8:
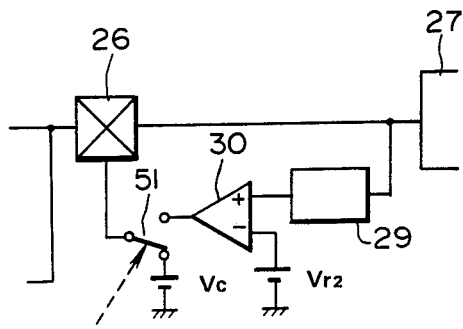
FIG. 8 is a block diagram showing an AGC circuit and elements around this circuit in a third embodiment of the present invention.

Thus, the second embodiment produces an effect substantially equivalent to that produced by the first embodiment insofar as the gain of the amplifier 43 can have the required gain. FIG. 8 shows a third embodiment of the present invention.

In this third embodiment, the output from the second level detection means 29 is applied to the non-inversion input terminal of the second comparator means 30, while the inversion input terminal of the second comparator means 30 receives the reference voltage Vr2. Between the second comparator means 30 and the gain control terminal of the variable gain amplifier 26 is connected an analog switch 51 of two-input and one-output type capable of being operated manually or in relation to a change in the light quantity control step. One of two input terminals of this analog switch 51 receives the output from the second comparator means 30, while the other input terminal receives a constant voltage Vc.

In this embodiment, when the central step or a step near the central step of the light quantity control has been selected, the AGC is operated with the output from the second comparator means 30 applied to the gain control terminal of the variable gain amplifier 26 through the analog switch 51.

On the other hand, when the light quantity is controlled manually, a constant voltage Vc is applied to the gain control terminal of the variable gain amplifier 26 through the above-mentioned analog switch 51 so as to open the feedback loop of the AGC circuit thereby maintaining the gain at a constant level, thus preventing the AGC circuit from taking part in the control of the light quantity.

Other portions of the arrangement, as well operation and effect, are the same as those of the first embodiment.

FIGS. 9 to 16 show a fourth embodiment of the present invention.

In contrast to the first and second embodiments in which the correcting operation by the AGC circuit in response to a charge in the light quantity control step is inhibited, the fourth embodiment features that the AGC is allowed to operate regardless of the light quantity control step whenever the full opening of the light control means 4 is detected, i.e., when a shortage of the light applied to the object is conceivable.

Figure 9:
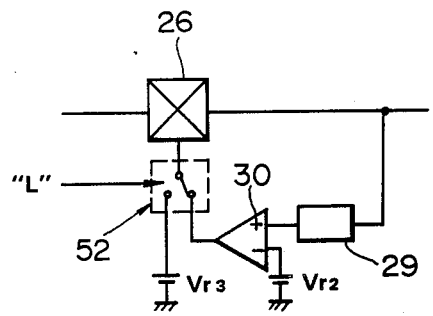
FIG. 9 is a block diagram showing an AGC circuit and elements around this circuit in a fourth embodiment of the present invention.

Similarly to the third embodiment, the fourth embodiment is so arranged that the output from the second level detection means 30 is applied to the non-inversion input terminal of the second comparator means 30, while the inversion input terminal of the second comparator means 30 receives the reference voltage Vr2. Between the second comparator means 30 and the gain control terminal of the variable gain amplifier 26 is disposed a switch means 52 of two-input and one-output type. One of the input terminals of the switch means 52 receives the output from the second comparator means 30 while the other input terminal receives a constant voltage Vr3 which is determined such as to make the gain of the variable gain amplifier 26 equal to 1. As shown in FIG. 9, the switch means 52 is connected to the second comparator means 30 in response to an "L" level signal which is applied to the control terminal thereof, so that the feedback loop is closed to allow ordinary AGC operation to be performed. On the other hand, when an "H" signal is received by the control terminal, the switch means 52 selects the voltage Vr3 so as to open the feedback loop, whereby the gain of the variable gain amplifier 26 is set at "1".

Figure 10:
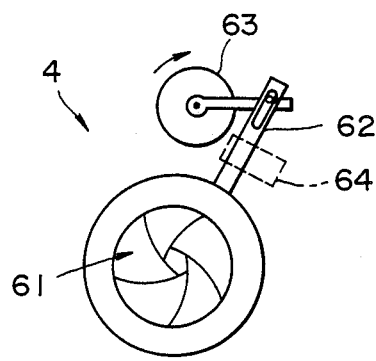
FIG. 10 is an illustration of a light control device of the type which incorporates iris blades used in the embodiment shown in FIG. 9.

The light control means 4 may be of the most ordinary type which uses iris blades as shown in FIG. 10.

More specifically, this light control means 4 may have iris blades 61, a link (arm) for driving the blades 61 in such a manner as to change the diameter of the aperture formed by the blades 61, and an iris motor 63 drivingly connected to the link 62. In operation, the output shaft of the motor 63 rotates within a given range of angle as electrical power is supplied to the iris motor 63, and the rotation of the motor output shaft is transmitted through the link 62 to the iris blades 61, whereby the diameter of the aperture formed by the blades 61 is changed to increase or decrease the quantity of light passing through the aperture.

A photo-coupler 64 disposed in the vicinity of the link 62 is capable of detecting that the iris blades have been moved to the full-open position.

Figure 12:
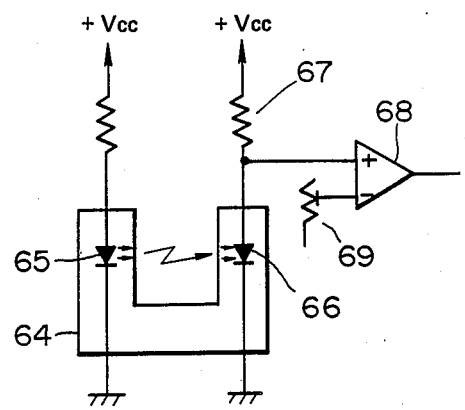
FIG. 12 is a circuit diagram illustrating the photo-coupler and elements around the photo-coupler.

FIG. 12 illustrates a circuit arrangement including the photo-coupler 64 and the photo-diode 66. As will be seen from this Figure, the photo-coupler 64 has an LED 65 and a photo-diode 66 which are arranged to oppose each other. A source voltage Vcc is applied both to the LED 65 and the photo-diode 66. The voltage developed between the photo-diode 66 and a load resistor 67 connected thereto is applied to the non-inversion input terminal of the load resistor 67. The inversion input terminal of the comparator 68 receives a reference voltage set by a reference voltage setting means 69. The photo-coupler 64 is arranged such that the LED 65 and the photo-diode 66 face each other across the path of the iris blades 61 such that the light emitted from the LED 65 can reach the photo-diode 66 only when the iris blades have been moved to the full-open position. i.e., such that the light is materially interrupted by the iris blades 61 when these blades are not in the full-open position.

Figure 11:
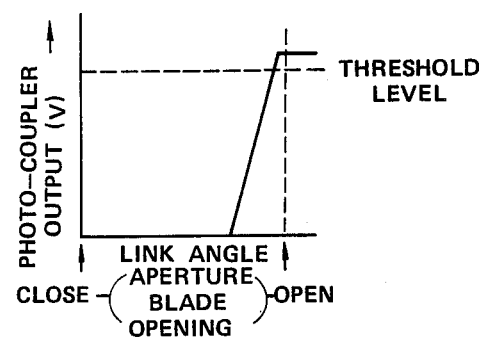
FIG. 11 is a diagram showing the relationship between a link angle in the light control device of FIG. 10 and the level of output from a photo-coupler.

The reference voltage applied to the comparator 68 is set at a threshold level as shown in FIG. 11, i.e., at a level slightly below the level of the output from the photo-coupler 64 as obtained when the iris blades 61 are in the full-open position, so that the comparator 68 can detect that the iris blades 61 are in the full-open position and produces a detection output level which is "L" in this embodiment. The "L" level signal from the comparator 68, representing that the iris blades 61 have been fully opened, is delivered to the switch means 52 so that the switch means 52 is connected to the second comparator means 30, thus allowing the AGC to commence the operation.

On the other hand, when the iris blades 61 are not in the full-open position, the comparator 68 produces an "H" signal so that the switch means 52 is connected to select the voltage Vr3, whereby the gain of the variable gain amplifier 26 is set at "1".

In order to stabilize the detecting operation in the region around the threshold level, the comparator 68 may be constructed as a so-called Schmidt trigger which is equipped with a feedback function.

Thus, in the fourth embodiment of the invention, the light control is performed by the ALC solely until the iris blades 61 are brought to the full-open position and the AGC is put into operation only after the iris blades 61 are fully moved to maximize the aperture diameter. Thus, the AGC function does not take part in the control of the light quantity when the light quantity is controlled within the range which is controllable by the iris blades 61.

The fourth embodiment may be modified such that the comparator 68 is built-in in the photo-coupler 64.

It is also possible to use, in place of the photo-coupler 64, a magnetic sensor which incorporates a hall element capable of detecting the presence or absence of a magnetic field. In such a case, a magnetic sensor is disposed in place of the photo-coupler 64 of FIG. 10 in the vicinity of the link 62 of the light control means 4, while a small-sized permanent magnet is disposed on the link 62, so that the full-open state of the iris blades 61 can be detected by the cooperation between the magnetic sensor and the permanent magnet. The magnetic sensor may be constructed in such a manner as to incorporate the comparator. Anyway, the magnetic sensor used in this modification is composed of an element which produces an output of "L" level upon detection of a full-open state of the iris blades 61. Other aspects of the operation are materially the same as those of the described embodiment which uses the photo-coupler. The structural features, operation and effect of this fourth embodiment other than described above are materially the same as those of the first embodiment.

Figure 13:
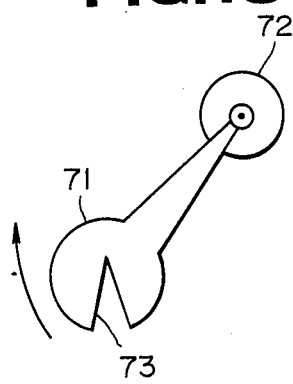
FIG. 13 is an illustration of an iris mechanism used in a modification of the embodiment shown in FIG. 9.

FIG. 13 shows another modification in which the iris blades 61 shown in FIG. 10 are substituted by an iris mechanism as shown in FIG. 13 as the light control means 4. This iris mechanism is composed of an iris link 71 and an iris motor 72 for rotating the iris link 71. The iris link 71 is provided at one end in the rotational direction with a wedge-shaped notch 73 which is adapted to be brought into alignment with the path of the illuminating light so as to cause a change in the quantity of the light passing through the notch 73.

This iris mechanism offers a high response speed by virtue of the reduced weight of moving parts. The means for detecting the full-open state of the iris blades used in combination with the blade-type iris mechanism may be used in combination with the iris mechanism having the notch in the iris link.

Figure 14:
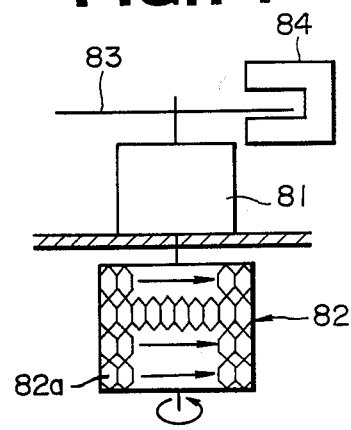
FIG. 14 is an illustration of an iris mechanism used in another modification of the embodiment shown in FIG. 9.

FIG. 14 shows another example of the iris mechanism having a honey-comb type construction. This iris mechanism comprises an iris motor 81, a honey-comb iris 82 secured to one end of the drive shaft of the iris motor 81, a rotation detecting plate 83 attached to the other end of the iris motor drive shaft, and detection means disposed in the vicinity of the rotation detecting plate 83 and capable of detecting the full-open state of the iris mechanism.

The honey-comb iris 82 has a construction which is composed of a multiplicity of tubular elements 82a each having a hexagonal cross-section. The inner surface of the tubular element 82a is suitably treated to provide a light shielding effect. The honey-comb iris 82 transmits the maximum light quantity when it is oriented such that the axes of the tubular element 82a extend in parallel with the axis of the illuminating light and the quantity of light transmitted therethrough is progressively decreased as the angle of inclination of the tubular elements 82a with respect to the optical axis of the illuminating light is increased.

By using this honey-comb iris 82, it is possible to improve the spectral characteristics in the core region and also in the peripheral region of the light beam. Theoretically, the honey-comb iris 82 can exhibit characteristic approximating the characteristic of an ND (Neutral Density) filter provided that the size of the hexagonal tubular elements can be reduced to approach zero. Thus, the honey-comb iris 82 has a possibility to provide an ideal light control characteristic.

Figure 15:
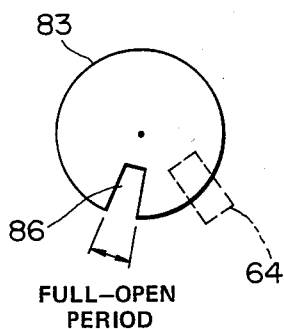
FIGS. 15 and 16 are illustrations of methods for detecting rotational position in the iris mechanisms shown in FIGS. 13 and 14, respectively.

FIG. 15 shows means for detecting the full open state of the iris of the honey-comb type. As will be seen from this Figure, the detecting means includes a detection means 84 having a photo-coupler 64 arranged to saddle the rotation detecting plate 83 which is provided with a notch 86 at its portion corresponding to the full-open state of the iris.

Figure 16:
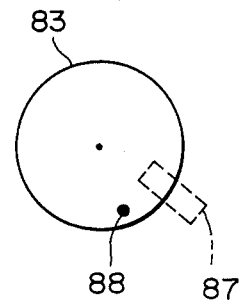

FIG. 16 shows an alternative means for detecting the full-open state of the iris. This detection means includes a magnetic sensor 87 disposed in the vicinity of the rotation detecting plate 83 and a small-sized magnet 88 which is provided on a portion of the rotation detection plate corresponding to the full-open state of the iris. Other portions are materially the same as those of the fourth embodiment.

Figure 17:
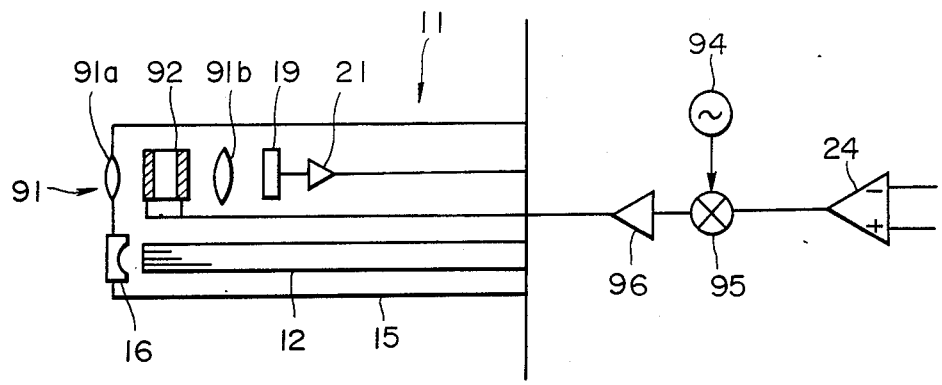
FIG. 17 is an illustration of an essential portion of an endoscope apparatus as a fifth embodiment of the present invention.
Figure 18:
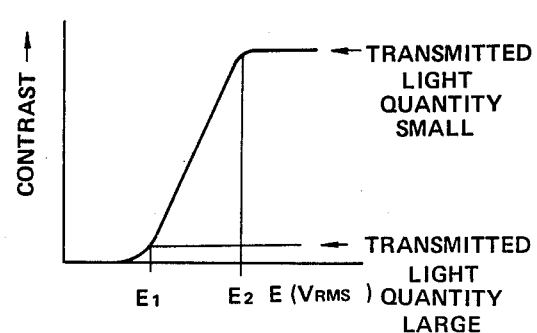
FIG. 18 is a diagram showing the control characteristic of a liquid crystal device as a light control used in the embodiment shown in FIG. 17.

FIGS. 17 and 18 illustrate a fifth embodiment of the present invention.

This embodiment is characterized in that the light control means is disposed in electronic endoscope 11 rather than in the light source unit 2.

As will be seen from FIG. 17, the insert section 15 of the electronic scope 11 is provided at the distal end thereof with an objective lens system 91 which is capable of focusing the image of the object on the SID 19. The objective lens system 91 is composed of objective lenses 91a and 91b which are arranged in optical alignment with each other with a liquid crystal 92 interposed therebetween.

In this embodiment, an oscillator 94 is associated with the signal processing device 22. The A.C. signal from the oscillator 94 is applied to the liquid crystal 92 through a gain control amplifier 95 and a liquid crystal driver 96. The gain of the gain-control amplifier 95 is controlled by the output signal from a comparator means equivalent to the first comparator means used in the first to fourth embodiments. As stated before, the light control means 4 is not provided in the light source unit 2. Other portions are materially the same as those of the first to fourth embodiments.

The operation of the fifth embodiment will be described hereafter.

The light of the maximum light quantity emitted from the light source unit 2 is applied to an object inside a human body through the light guide 12 and the light distribution lens 16. The light reflected by the object is focused through the objective lens system 91 to form an image of the object on the SID 19. The quantity of the reflected light reaching the SID 19 is controlled by the liquid crystal 92 in the objective lens system 91 as the light passes through the system 91. The object image formed on the SID 19 is photoelectrically converted into an image signal by the SID 19.

The image signal thus obtained is processed in the same manner as those in the preceding embodiments so that a base band image signal is obtained. A part of this signal is delivered to the first comparator means 24 through the first level detection means 23 so that an iris control signal representing the level of brightness of the image signal is derived from the comparator means 24.

In this embodiment, the light control means comprises the liquid crystal 92. The control characteristic of the liquid crystal 92 will be explained with reference to FIG. 18 in which the axis of the abscissa represents the voltage applied while the axis of the ordinate represents the contrast of the image. The quantity of light transmitted through the liquid crystal 92 is controllable through the control of the effective value (RMS) of the A.C. voltage applied across the liquid crystal 92. Thus, any desired level of light transmission between full transmission and full interruption can be obtained by an arrangement for varying the voltage applied across the liquid crystal 92 between $E_1$ and $E_2$ in terms of effective value ($V_{RMS}$).

The amplitude of the A.C. signal derived from the oscillator 94 is controlled by an iris control signal from the first comparator means 24 so as to form the voltage level between $E_1$ and $E_2$ ($V_{RMS}$) as shown in FIG. 18, thereby effecting the control of the liquid crystal 92. Namely, when the intensity of the light reflected from the object is high so as to form a bright image, the voltage applied to the liquid crystal 92 is changed towards the voltage level $E_2$ so as to reduce the quantity of light reaching the SID 19 through the liquid crystal 92. Conversely, when the intensity of the reflected light is low so that the image is dark, the voltage is controlled in such a direction as to increase the quantity of light reaching the SID 19 through the liquid crystal 92. This control system therefore has a closed feedback loop so that an automatic light control means is obtained.

Other portions of construction, operation and effect are the same as those in the first to fourth embodiments.

Figure 19:
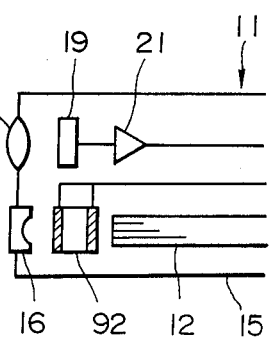
FIG. 19 is an illustration of an essential portion of an endoscope apparatus as a sixth embodiment of the present invention.

FIG. 19 illustrates a sixth embodiment of the present invention.

This embodiment is characterized in that the liquid crystal 92 similar to that used in the fifth embodiment is disposed between the light-emanating end of the light guide 12 and the light distribution lens 16 rather than on the front side of the SID 19.

In this embodiment, therefore, the light quantity control is effected on the light which is applied to the object.

Other portions of the construction, operation and effect are the same as those of the fifth embodiment.

Although in the fifth and sixth embodiments the light control means incorporating the liquid crystal 92 is disposed on the end of the insert section 15 of the electronic endoscope 11, this is not exclusive and the arrangement may be such that the same light control means may be associated with the light source unit or may be provided on the light-receiving end of a television camera which is adapted to be secured to the eyepiece of a fiber scope.

Figure 20:
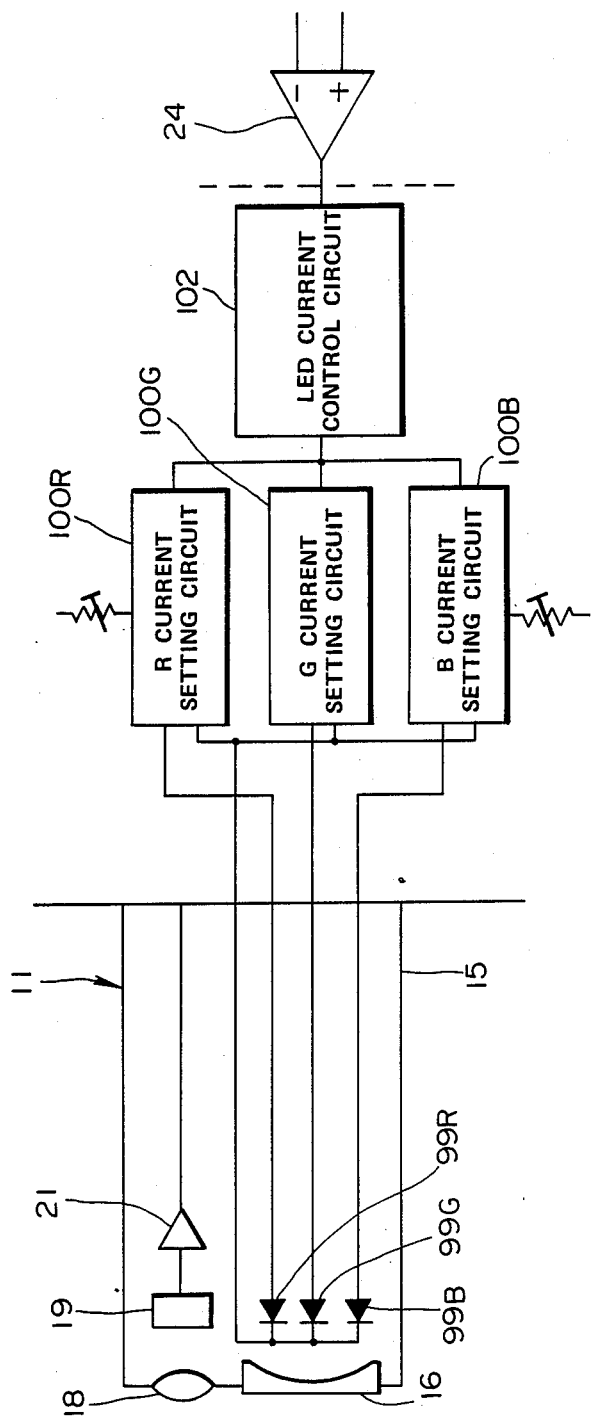
FIG. 20 is an illustration of an essential portion of an endoscope apparatus as a seventh embodiment of the present invention.

FIG. 20 shows a seventh embodiment of the present invention.

This embodiment is an electronic scope which incorporates a solid light source such as an LED in place of the lamp of the light source unit 2. The LED is capable of emitting light of an intensity proportional to the electric current flowing therethrough. It is therefore possible to construct a very simple controllable light source by making use of an LED, so as to eliminate the necessity for a specific light control means such as a liquid crystal or a mechanical iris mechanism. The following description will be made on an assumption that a monochromatic (black and white) illuminating light is used.

As will be seen from FIG. 20, there are three LEDs 99R, 99G and 99B, capable of emitting red (R), green (G) and blue (B) light disposed on the inner side of the light distribution lens 16 provided on the distal end of the insert section 15 of the electronic scope 11. These LEDs 99R, 99G and 99B are respectively connected to an R current setting circuit 100R, a G current setting circuit 100G and a B current setting circuit 100B which are provided in the signal processing device 22. These current setting circuits 100R, 100G and 100B are connected to an LED current control circuit 102. The LED current control circuit 102 is capable of controlling the total current on all the LEDs in accordance with the iris control signal derived from the first comparator means 24. In each current setting circuit, the LED current is fixed only for the G current setting circuit 100G, whereas the R current setting circuit 100R and the B current setting circuit 100B are arranged to allow the adjustment of the respective LED currents so as to enable white balance control. The total LED current supplied to the group of R, G and B LEDs 99R, 99G and 99B after the completion of the balance adjustment is controlled by the LED current control circuit 102 in accordance with the iris control signal from the first comparator means 24, whereby the light quantity is controlled with balanced white light.

Namely, when the intensity of light reflected from the object is so high as to form too bright an image, the iris control signal from the first comparator means 24 is delivered to the LED current control circuit 102 so as to lower the luminance of the LEDs. Conversely, when the intensity of light reflected from the object is so low as to form too dark an image, the LED current control circuit 102 is controlled by the output from the first comparator means 24 so as to increase the luminance of the LEDs. Thus, a closed loop with feedback is also formed in this embodiment, thus realizing a stable automatic light control function.

When a color image is to be obtained by simultaneous processing of different color signals obtained from white illuminating light, a color filter may be used which has color filter elements capable of transmitting light of R, G and B wavelengths and arranged in a mosaic manner.

It is also possible to obtain a color image by a sequential type imaging and processing systems in which LEDs 99R, 99G and 99B are made to illuminate in a time-series manner.

Other portions of construction, operation and effect are the same as those of the first to fourth embodiments.

Figure 21:
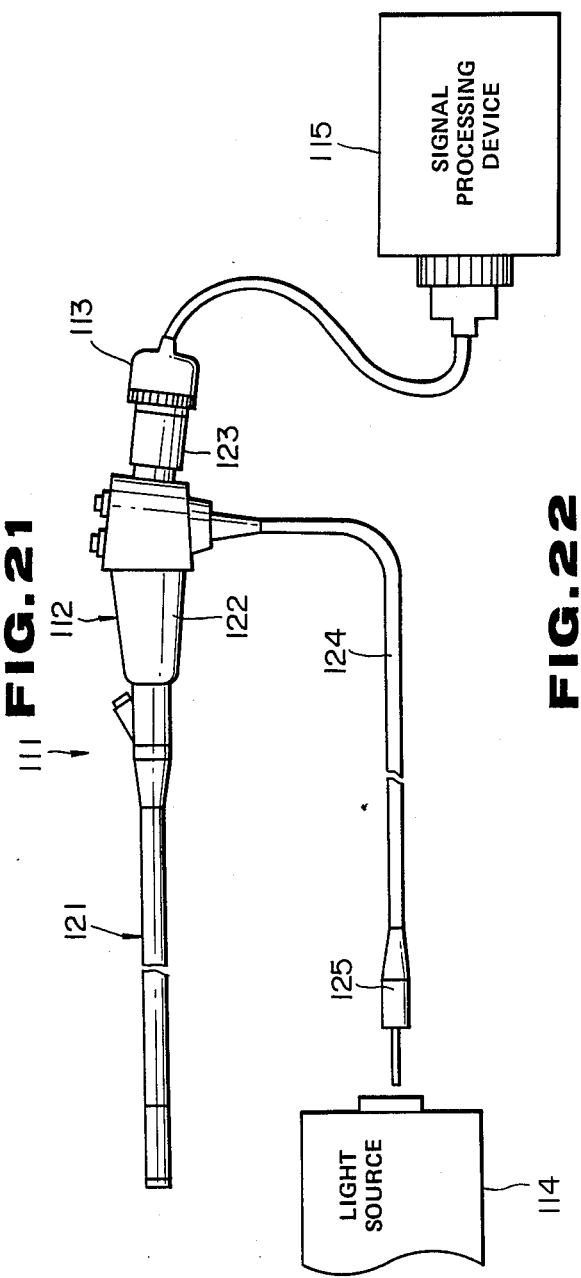
FIG. 21 is an illustration of the whole of an endoscope apparatus as an eighth embodiment of the present invention.

An eighth embodiment of the invention will be described with specific reference to FIGS. 21 and 22.

The endoscope apparatus of this embodiment, generally denoted by a numeral 111, has a fiber scope 112, a small-sized television camera 113 detachably secured to the eyepiece 123 of the fiber scope 112, a light source unit 114 to which the fiber scope 112 is connected, and a signal processing device 115 to which the television camera 113 is connected.

The fiber scope 112 has an elongated flexible insert section 121, a manipulating section 122 connected to the rear end of the insert section 121, an eyepiece 123 provided on the rear end of the manipulating section 122, a light guide cable 124 extended from one lateral side of the manipulating section 122, and a connector provided on the end of the light guide cable 124 and connected to the light source section 114.

Figure 22:
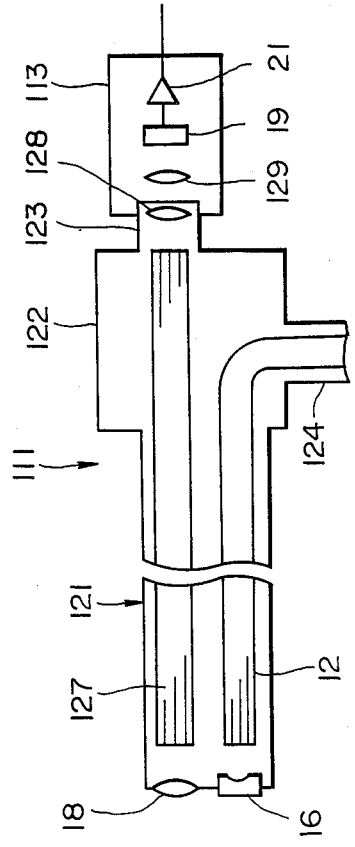
FIG. 22 is an illustration of an essential portion of the endoscope apparatus shown in FIG. 21.

As will be seen from FIG. 22, a light distribution lens 16 and an objective lens 18 are provided on the end of the insert section 121. A light guide 12 connected to the rear side of the light distribution lens 16 is extended through the insert section 121, manipulating section 122 and the light guide cable 124 and is connected to the connector 125. An image guide 127 composed of a fiber bundle has an end surface which is disposed at the focal plane of the objective lens 18. The image guide 127 extends through the insert section 121 so that its rear end opposes the eyepiece lens 128 in the eyepiece section 123. The image of the object focused by the objective lens 18 is transmitted to the eyepiece section 123 through the image guide 127 so as to be observed through the eyepiece section 123.

On the other hand, the television camera 113 has an image-forming lens 129 which receives the light from the eyepiece section 123 and capable of forming an image of the object, an SID 19 disposed on the focal position of the image-forming lens 129, and an amplifier 21 capable of amplifying the signal from the SID 19. The television camera 113 operates in accordance with a drive signal derived from the signal processing device 115 which produces an image signal by processing the video signal derived from the SID 19. The signal processing device 115 may be of the type similar to the signal processing device 22 capable of being connected to an electronic scope 11 used in the preceding embodiments. In such a case, the television camera 113 may be connected to the signal processing device 22 in place of the electronic scope 11, or the signal processing device 22 is used exclusively for the television camera 113.

Any type of light control means used in the first to seventh embodiments can be used as the light control means in the eighth embodiment.

In the described embodiment, the light source section 114 and the signal processing device 115 are constructed as separate devices. In such a case, needless to say, the light source section 114 and the signal processing device 15 are connected to each other through cables and connectors which are not shown so as to operatively connect the light control means and the AGC circuit.

Although the sequential illuminating type electronic endoscope apparatus has been described, it will be clear to those skilled in the art that the invention can equally be applied to a system in which a color image is formed under illumination with white light by using an electronic scope which is provided with a color filter disposed in front of the SID 19 and having filter elements of respective colors arranged in a mosaic manner. The invention also is applicable to a system in which a TV camera having an SID is connected to the eyepiece portion of a rigid endoscope.

It is also to be understood that the described embodiment is applicable to the case where the ALC function is omitted, i.e., in such a system that the light quantity is controlled only by an AGC function and manual operation.

Although a reflection type endoscopes have been described specifically, the invention can equally be applied to an endoscope which is designed to enable an object to be observed by processing image signals obtained from the light transmitted through the object rather than the light reflected by the same.

As will be understood from the foregoing description, the present invention provides an endoscope output signal control device, as well as an endoscope apparatus making use of the same, which can operate with an amplified dynamic range and with a quick response to an input for changing the light quantity, without substantially affecting the light control function of the endoscope.

Although the invention has been described in specific terms, it is to be understood that the described embodiments and modifications are only illustrative and various changes and modifications are possible without departing from the spirit and scope of the invention which are limited solely by the appended claims.

What is claimed is:

1. An endoscope output signal control device comprising:
   light quantity varying means for varying a quantity of light incident to an imaging means for forming an endoscopic image;
   light quantity setting means for variably setting the quantity of incident light by driving said light quantity varying means;
   automatic gain control means for conducting control to maintain a signal from said imaging means substantially at a constant level; and
   automatic gain control eliminating means for eliminating, at least when a level of the signal from said imaging means is within range controllable by said light quantity varying means, any influence of said automatic gain control means on a change in the level of said signal caused by a change in a level of light quantity set by said light quantity setting means.

2. An endoscope output signal control device according to claim 1, further comprising automatic light control means for driving said light quantity varying means to control the quantity of said incident light in such a manner as to maintain said signal from said imaging means substantially at a constant level.

3. An endoscope output signal control device according to any one of claims 1 or 2, wherein said automatic gain control eliminating means includes command value changing means for changing a command value of said automatic gain control means in accordance with information concerning the level of the light quantity set by said light quantity setting means.

4. An endoscope output signal control device according to any one of claims 1 or 2, wherein said automatic gain control eliminating means includes transfer function changing means for changing a transfer function of a feedback element of said automatic gain control means in accordance with information concerning the level of the light quantity set by said light quantity setting means.

5. An endoscope output signal control device according to claim 4, wherein said transfer function changing means includes offset voltage changing means for changing an offset voltage of a feedback element of said automatic gain control means in accordance with information concerning the level of the light quantity set by said light quantity setting means.

6. An endoscope output signal control device according to any one of claims 1 or 2, wherein said automatic gain control eliminating means includes means for opening a feedback loop of said automatic gain control means when information concerning the level of the light quantity set by said light quantity setting means indicates that a set light quantity falls outside a predetermined range.

7. An endoscope output signal control device according to any one of claims 1 or 2, wherein said automatic gain control eliminating means includes means for opening a feedback loop of said automatic gain control means when the level of the signal from said imaging means falls within a range controllable by said light quantity varying means.

8. An endoscope output signal control device according to claim 2, wherein said automatic gain control means is provided on an output side of said automatic light control means.

9. An endoscope output signal control device according to claim 2, wherein said light quantity setting means has means for varying a command value of said automatic light control means to vary the quantity of the incident light.

10. An endoscope output signal control device according to any one of claims 1 or 2, wherein said light quantity varying means includes means for varying a quantity of illuminating light for illuminating an endoscopic observation object.

11. An endoscope output signal control device according to claim 10, wherein said light quantity varying means includes an iris disposed in a path of the illuminating light.

12. An endoscope output signal control device according to claim 11, wherein said iris is provided in a light source means for supplying the illuminating light to an endoscope.

13. An endoscope output signal control device according to claim 11, wherein said iris includes a liquid crystal disposed on an illuminating light emanating end at an end of said endoscope.

14. An endoscope output signal control device according to claim 10, wherein said light quantity varying means includes means for controlling the quantity of light emitted from a light source for emitting the illuminating light.

15. An endoscope output signal control device according to any one of claims 1 or 2, wherein said light quantity varying means includes an iris disposed between an object and said imaging means.

16. An endoscope output signal control device according to claim 15, wherein said iris includes a liquid crystal.

17. An endoscope apparatus comprising:
an endoscope unit including an elongated insert section provided at an end with an observation window and an image forming optical system for receiving light reflected from an object to focus an image of said object;
imaging means for forming said image of said object focused thereon through said image forming optical system;
signal processing means for conducting video signal processing on a signal derived from said imaging means;
illuminating means for supplying illuminating light to a visual field of said image forming optical system;
light quantity varying means for varying a quantity of light incident to said imaging means for forming an endoscopic image;
light quantity setting means for variably setting a quantity of incident light by driving said light quantity varying means;
automatic gain control means for conducting control to maintain the signal from said imaging means substantially at a constant level; and
automatic gain control eliminating means for eliminating, at least when a level of the signal from said imaging means is within a range controllable by said light quantity varying means, any influence of said automatic gain control means on a change in the level of said signal caused by a change in a level of light quantity set by said light quantity setting means.

18. An endoscope apparatus according to claim 17, further comprising automatic light control means for driving said light quantity varying means to control the quantity of said incident light in such a manner as to maintain said signal from said imaging means substantially at a constant level.

19. An endoscope apparatus according to any one of claims 17 or 18, wherein said imaging means is a solid-state device disposed in the end of the insert section of the endoscope unit at a focal position of said image forming optical system.

20. An endoscope apparatus according to any one of claims 17 or 18, wherein said endoscope unit further includes an eyepiece portion provided on a rear end of said insert section and an image transmitting means for transmitting to said eyepiece portion the image of the object focused by said image forming optical system, and wherein said imaging means includes a television camera detachably connected to said eyepiece portion.

21. An endoscope apparatus according to any one of claims 17 or 18, wherein said illuminating means includes an illuminating window provided in the end of said insert section of said endoscope unit, a light source provided separately from said endoscope unit, and illuminating light transmitting means for transmitting the illuminating light from said light source to said illuminating window.

22. An endoscope apparatus according to any one of claims 17 or 18, wherein said illuminating means includes an illuminating window provided in the end of said insert section of said endoscope unit and a light source provided on an inner side of said illuminating window.

* * * * *